(12) United States Patent
Obeid et al.

(10) Patent No.: US 11,441,601 B1
(45) Date of Patent: Sep. 13, 2022

(54) BLOOD PUMP BEARING SYSTEM WITH OPTIMIZED GEOMETRY, MATERIALS, AND MANUFACTURING METHOD

(71) Applicant: RBTS Inc., Phoenixville, PA (US)

(72) Inventors: Victor Obeid, Collegeville, PA (US); Michael D. Neary, Bryn Mawr, PA (US); Edward Marlinski, Lansdale, PA (US)

(73) Assignee: RBTS Inc., Phoenixville, PA (US)

( * ) Notice: Subject to any disclaimer, the term of this patent is extended or adjusted under 35 U.S.C. 154(b) by 0 days.

(21) Appl. No.: 16/953,531

(22) Filed: Nov. 20, 2020

Related U.S. Application Data

(60) Provisional application No. 62/951,825, filed on Dec. 20, 2019.

(51) Int. Cl.
| | | |
|---|---|---|
| F16C 17/10 | (2006.01) | |
| F04D 29/046 | (2006.01) | |
| A61M 60/824 | (2021.01) | |
| F16C 17/02 | (2006.01) | |

(52) U.S. Cl.
CPC ........... *F16C 17/10* (2013.01); *A61M 60/824* (2021.01); *F04D 29/046* (2013.01); *F16C 17/028* (2013.01); *F16C 2206/56* (2013.01); *F16C 2208/58* (2013.01); *F16C 2316/18* (2013.01)

(58) Field of Classification Search
CPC ...... F16C 17/028; F16C 17/047; F16C 17/10; F16C 17/102; F16C 17/105; F16C 17/1075; F16C 17/33; F16C 33/043; F16C 33/20; F16C 33/201; F16C 2316/18; A61M 60/818; A61M 60/824; A61M 60/825
See application file for complete search history.

(56) References Cited

U.S. PATENT DOCUMENTS

| | | | | |
|---|---|---|---|---|
| 5,211,546 | A | * | 5/1993 | Isaacson ............. A61M 60/824 417/356 |
| 10,722,627 | B1 | * | 7/2020 | Obeid ................. A61M 60/818 |
| 10,918,774 | B2 | * | 2/2021 | Stanfield ............. A61M 60/122 |
| 2020/0368415 | A1 | * | 11/2020 | Antaki ................ F16C 32/0425 |

OTHER PUBLICATIONS

Noria Corporation, Lubrication Regimes Explained, obtained Sep. 22, 2021.*

* cited by examiner

*Primary Examiner* — James Pilkington
(74) *Attorney, Agent, or Firm* — Joseph E. Maenner; Maenner & Associates, LLC

(57) ABSTRACT

A rotor bearing system includes an inner bearing component and an outer bearing component. One of the bearing components includes at least three protrusions sized to form a close running proximity to the remaining component. A bearing gap between the inner bearing component and the outer bearing component is sized to exclude the entry of red blood cells between the bearing components during operation of the rotor bearing system and causing the bearing to operate in an elasto-hydrodynamic regime of mixed- or boundary-lubrication.

22 Claims, 14 Drawing Sheets

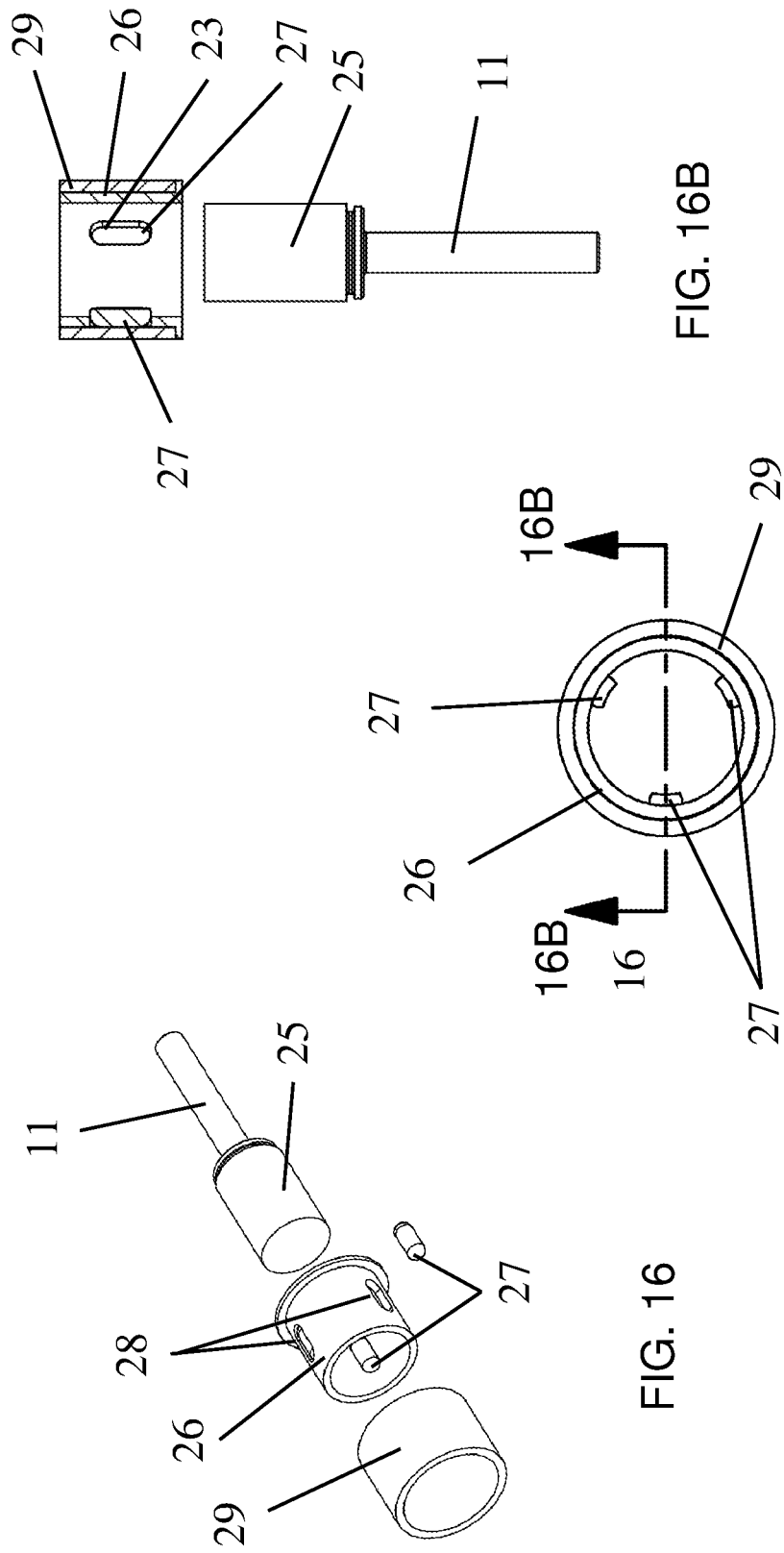

BLOOD PUMP BEARING SYSTEM WITH OPTIMIZED GEOMETRY, MATERIALS, AND MANUFACTURING METHOD

CROSS-REFERENCE TO RELATED APPLICATION

The present application claims the benefit of U.S. Provisional Patent Application Ser. No. 62/951,825, filed on Dec. 20, 2019, which is incorporated herein by reference in its entirety.

FIELD OF THE INVENTION

This invention relates to the field of pumps. In particular, this invention is drawn to bearings for various blood pump rotor and stator configurations.

BACKGROUND OF THE INVENTION

Mechanical circulatory support systems (MCSS) from a variety of manufacturers have been used to treat many types of heart function degradation over the past several decades. This includes, but is not limited to, the class of devices known as ventricle assist devices or VADs. Such devices can be axial, radial, or mixed flow pumps designed either for intrathoracic, intracardiac, pericardiac, intra-aortic, or intra-arterial implantation. Such devices can be characterized by rotary, reciprocating, oscillatory or linear motion and can be steady state or pulsatile in function. One recurring problem with the current pump designs is thrombus formation within the pumps, often starting in areas of stasis formed by the bearings and/or bearing support structure. A second recurring problem is blood hemolysis due to excessive shear stress being applied to the red blood cells as they pass through the rotor bearing system.

It would be beneficial to provide a bearing for blood pumps that solves these problems.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Through application of bearing geometry to create an open annulus through-flow design which blood flow continually flushes, the present invention reduces or eliminates stasis within the pump bearings, thereby solving the problem of thrombus formation. Additionally, the inventive bearing geometry supports an elasto-hydrodynamic lubrication layer that prevents red blood cells from entering the running gap between bearing and journal, thereby reducing or eliminating hemolysis within the bearing system. The use of select pairs of advanced engineering materials and tribological pressure-velocity (PV) analysis for such materials pairs provides a zero-wear to very-low wear bearing system.

This invention pertains to pumps, heart assist pumps, in particular the bearings systems required to successfully support, locate, and guide a pump's moving components with respect to a pump's stationary components. In an exemplary embodiment, hemispherical and cylindrical domes (or protuberances) are used to create a space designed for through-flushing between the moving and non-moving pump components, to prevent thrombus while incorporating favorable geometry beneficial to sliding-surface bearing operation. Additionally, this invention addresses the problems inherent in bearing fabrication from certain engineering materials preferred for bearings such as hard ceramics or engineered plastics. Machining precise complex geometries from these specialized materials within miniature internal diameters of cylinders, conical voids, or spherical voids used in bearing designs can be impossible or extremely time consuming and expensive. Notably, ceramic materials must be ground, honed and lapped to final size and shape. Likewise, it can be difficult to machine features with tight tolerances in engineered plastics due to deformation and heat generation while under tool cutting loads. Additionally, for certain specialty bearing materials, particular mechanical properties such as tensile strength, may be inferior to that of metals for a given component size, component shape or loading direction. These shortcomings are in contrast to metals such as stainless steel or titanium which can be worked with multi-axis machine tools to produce highly intricate part geometries at tight tolerance and with fine surface finishes, all critical to success for blood wetted components within blood pumps. The present invention provides a bearing design that incorporates the best features of both easy to machine metals and difficult to machine specialty materials. Such materials are then used within a self-flushing and long-lasting bearing design, which provides superior performance in blood wetted applications.

BRIEF DESCRIPTION OF THE DRAWINGS

The present invention is illustrated by way of example and not limitation in the figures of the accompanying drawings. In these figures the bearings and journals are illustrated as standalone components without the illustration of non-bearing pump components such as the rotor body, stator attachments, pump impeller, etc. Furthermore, like references indicate similar elements across multiple illustrations. Illustrations of the journal are often shown with a mounting pin 11 that can be mechanically attached to the rotor by fasteners, welding, adhesives, or other methods.

In the drawings:

FIG. 16 is an exploded perspective view of a cylindrical bearing fabricated using ceramic or engineered plastic hemi-cylinders captured in the retainer ring to create the bearing surfaces in the outer bearing component.

FIG. 16A is an end elevational view of the bearing of FIG. 16.

FIG. 16B is a sectional view of the bearing of FIG. 16A taken along lines 16B-16B of FIG. 16A.

DETAILED DESCRIPTION

Figure 1:
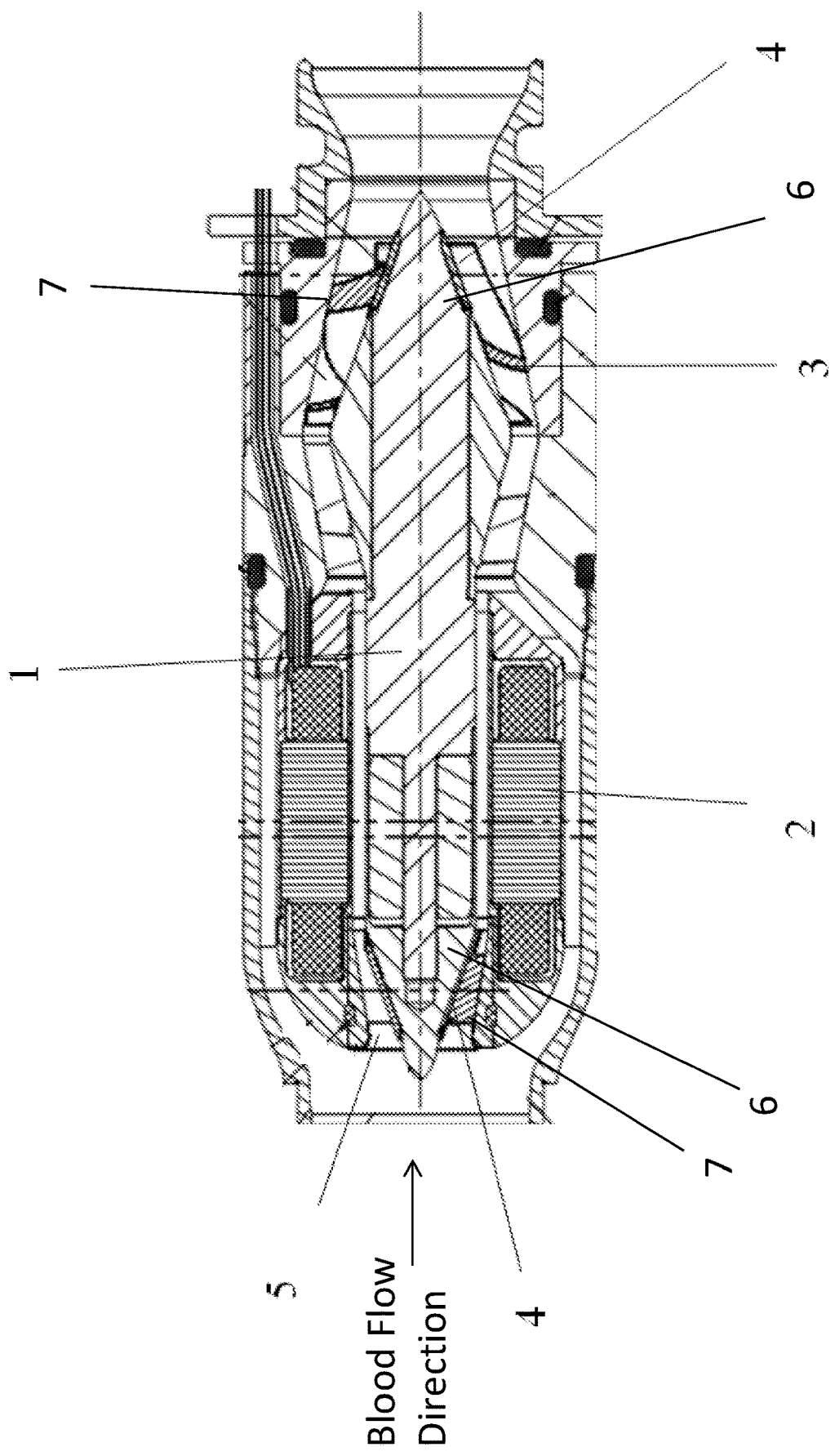
FIG. 1 illustrates the cross section of a typical rotary blood pump with dual conical bearings for the centrally located rotor.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

Bearings as described in this invention can be deployed in traditional rotary pump configurations with a rotor 1 located on the device central-axis with a surrounding non-rotating stator 2. Alternatively, the bearings can be used in out-runner style pumps where the centrally located stator is stationary and the radially outward rotor rotates relatively to the fixed stator. Moreover, these bearings can be used in eccentrically notating, oscillating or linear motion devices. In FIG. 1, the LVAD rotor, situated along the pump centerline is provided with impeller vanes 3 to induce fluid flow and create pressure rise. It is configured with hydrodynamic conical bearing surfaces 4 and conical journals 6 at either end of the rotor to locate, support, and guide the rotor both axially and radially during operation. This typical bearing design utilizes support struts 7 across the flow path to fix the stationary bearing component in the blood flow path. The existence of the fixed bearing component and the struts in the flow path reduce the annular space 5 through which blood flows, and such fixed bearings and struts can be sources of flow stasis, which in turn can lead to thrombus formation near the bearings.

Figure 2:
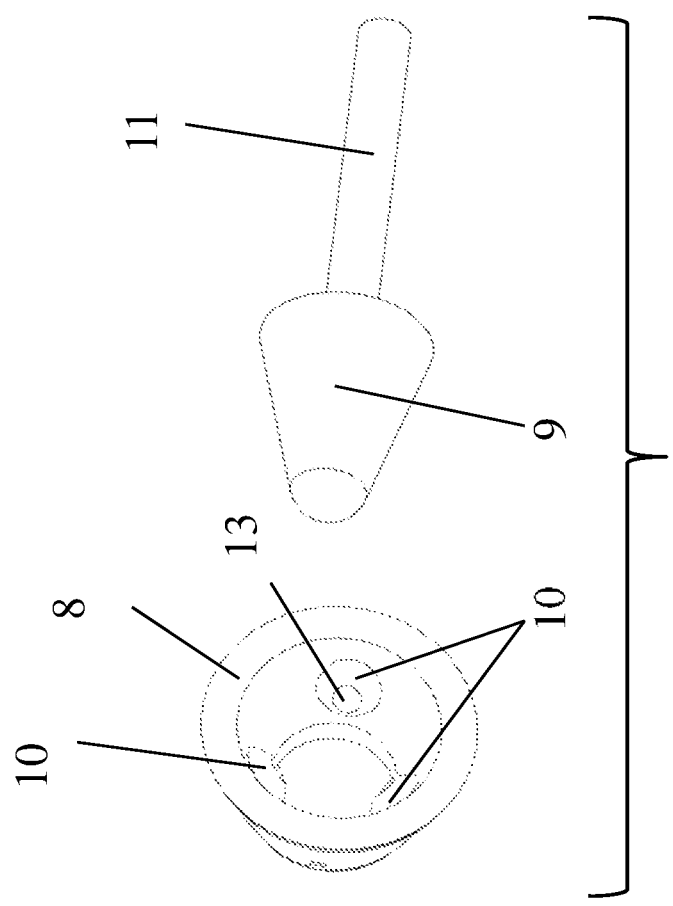
FIG. 2 is an exploded side elevation view of a smooth conical journal and a mating conical bearing with spherical domes.
Figure 11:
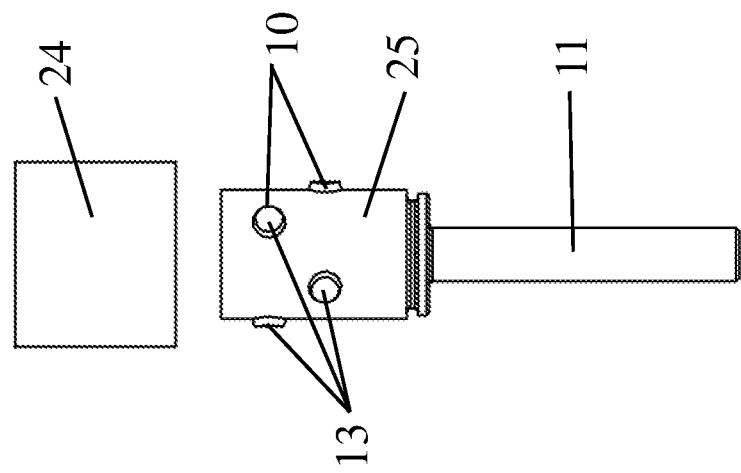
FIG. 11 is an exploded side elevation view of a cylindrical bearing using spherical protrusions as the bearing surfaces.

The bearing implementations of the present invention can have a generally conical shape of the bearing components 8, 9 as illustrated in FIG. 2, that provides rotor support in both radial and axial directions to react hydraulic loads from the pumping action, centrifugal loads from rotating imbalance, and magnetic loads from rotor/stator offset. Alternatively, the bearing components can have a generally cylindrical shape 24, 25, as shown in FIG. 11, that reacts to radial forces and moments but not axial thrust force.

Referring back to FIG. 2, the load carrying surface area, or contact area 13, between a journal 9 and bearing 8 is sized to generate an acceptable level of bearing stability, damping, and a favorable pressure-velocity (PV) value between the two mating bearing components. The calculation of a pressure-velocity value for combinations of typical bearing materials is a technique common to the study of tribology in order to predict the success of a bearing system versus its expected loading and rotational speed operating envelope. In general, empirical pin on disk testing of material pair combinations are conducted while varying the applied pressure and relative speeds in order to chart wear rates. Higher wear rates are associated with higher pressures or higher relative velocities between the two surfaces in sliding contact. Low PV values, for known combinations of preferred bearing materials, can result in zero-wear to extremely low-wear rates of the fixed and rotating bearing system components.

Figure 3:
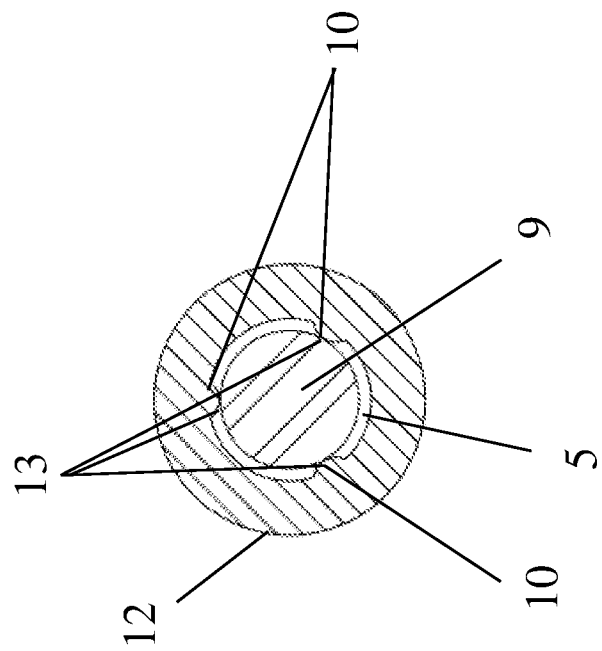
FIG. 3 is a radial cross section of a conical journal and a mating conical bearing with spherical domes.
Figure 4:
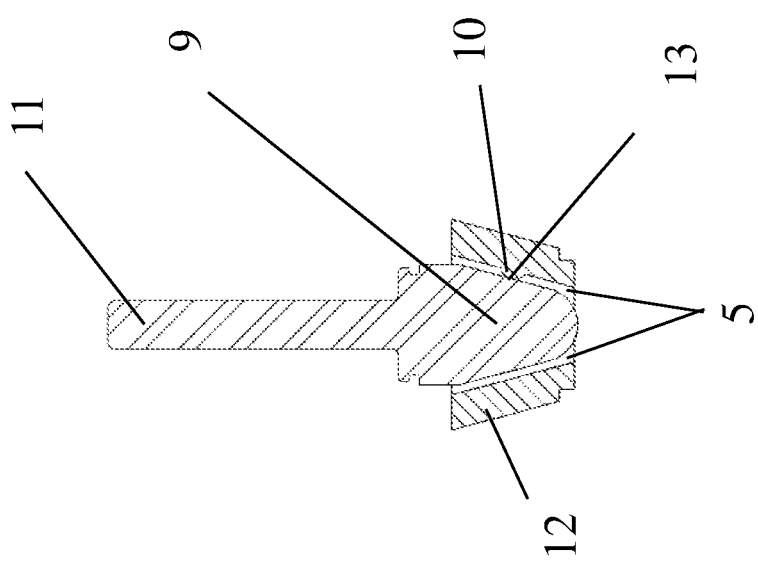
FIG. 4 is an axial cross section of a conical journal and a mating conical bearing with spherical domes.

The use of protruding spherical domes 10 serves to separate the journal 9 and bearing 8, thereby creating space for blood to flow and resulting in smaller point contact areas between the journal 9 and bearing 8, as illustrated in FIGS. 2 through 4. Use of protruding domes 10 creates an annulus 5, allowing flushing flow, and also which eliminates the stationary bearing component and support struts from the blood flow path. This embodiment of the invention illustrated in FIG. 4 makes use of protrusions 10 formed onto the inner wall of the bearing surface. The dome shaped protrusion 10 is advantageous because the natural taper of the spherical dome protrusion 10 towards the point of contact creates a converging wedge in all directions about the point of contact, regardless of the angle of approach of the blood velocity vector. Hydrodynamic bearing design requires a converging wedge shape in order for successful hydrodynamic film establishment and hydrodynamic bearing operation.

The various implementations presented below are purposefully designed for a tight sliding-fit clearance operation between the journal or slider and raised protrusions on the mating, moving bearing component, thereby causing the bearing system to operate in an elasto-hydrodynamic regime of mixed- or boundary-lubrication. Such tight clearance operation excludes the entry of red blood cell between the bearing running surfaces. Such clearances for hydrodynamic bearings or elasto-hydrodynamic bearings could be in the range up to 0.025 to 0.051 mm (0.001 or 0.002 inches), or more preferably up to 0.013 mm (0.0005 inch) clearance, or most preferably 0.0005 to 0.0023 mm (0.000020 to 0.000090 inches) clearance.

FIG. 3 provides a radial cross section of a three-dome bearing 12 with the section plane located through the three spherical domes 10 at the point of contact with the centrally-located smooth conical journal 9. The physical contact area 13 between the conically shaped journal 9 and the three domes 10 can range from three point contacts to three very small areas, or lands, of contact. Such contact areas can be formed by mechanical deformation, machine tool cutting, or abrasive methods in order to create a conformal, tight sliding-fit clearance between the parts.

A comparison can be drawn between the annular open space 5 for blood flow versus the cross-sectional area allocated to the domes 10. The majority of the annular area 5 through the bearing is open to flow and flushing while the area occluded by the spherical domes 10 is minimal. The ratio of open space to occluded area is determined with respect to the hydrodynamic requirements of the specific pump, and the bearing contact area sizing requirements FIG. 4 illustrates an axial cross section of a bearing utilizing spherical domes 10 mating to a smooth conical journal 9 surface with the blood flow path 5 between the journal 9 and bearing 12, past the dome 10 where the bearing contact area 13 is sized to support the loading generated by the pump rotor. Either component may be rotatable with respect to the other fixed component, dependent upon the pump rotor and motor design.

Figure 5:
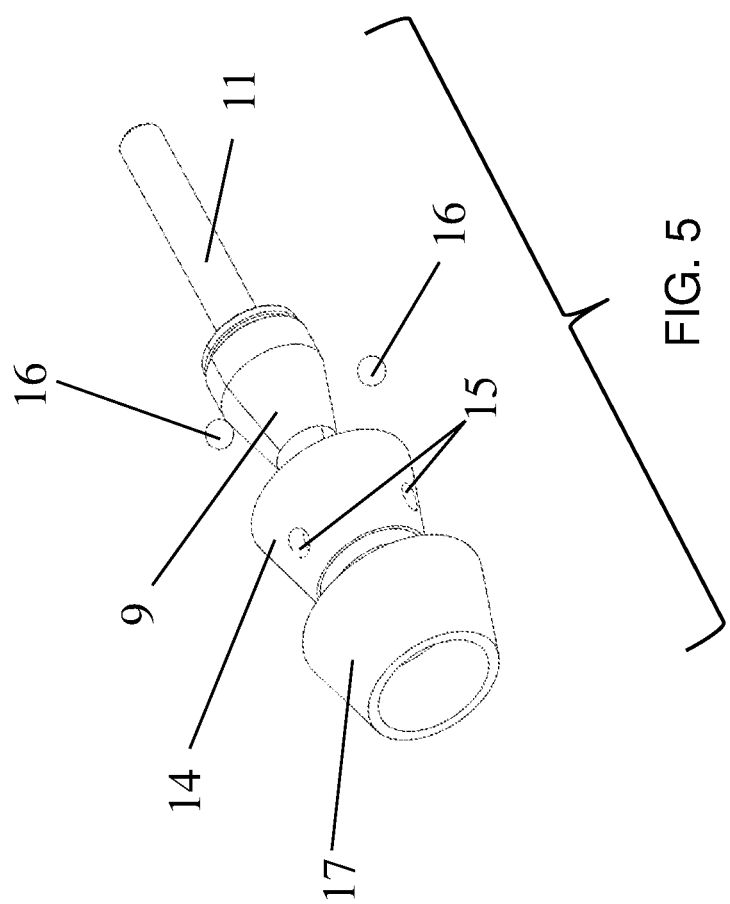
FIG. 5 is an exploded side elevation view of a multi-component multi-material conical bearing constructed with spheres and retaining ring.
Figure 6:
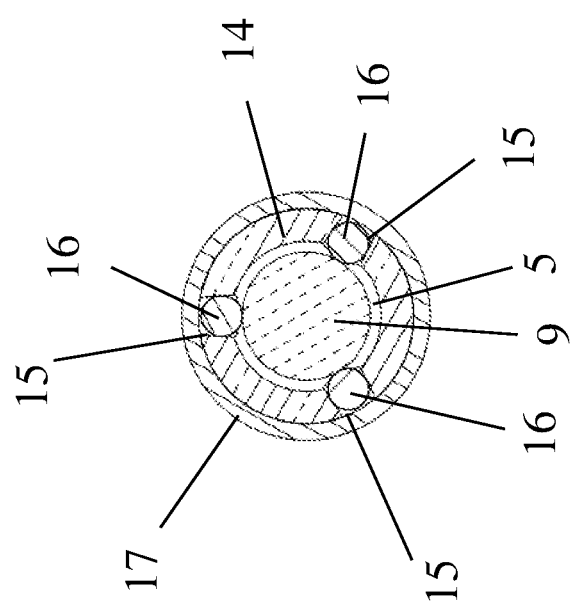
FIG. 6 is a radial cross section of a multi-component multi-material conical bearing constructed with spheres and retaining ring.

A second embodiment of the invention is illustrated in FIGS. 5 and 6. Recognizing that multi-axis machining of miniature internal features and surfaces within a narrow-bottomed internal diameter is difficult, particularly when viewed with respect to the need for superior surface finishes and close machining tolerances, a bearing system was developed to incorporate separately manufactured components of desirable, but difficult to machine, bearings materials. This includes the class of materials generally called ceramics and particularly ceramics such as but not limited to sapphire, aluminum oxides, zirconium oxide, yttria-stabilized zirconium oxide (Y-TZP), silicon carbide, and also engineered plastics such as PEEK (poly ether ether ketone), Filled-PEEK, UHMWPE (ultra-high molecular weight polyethylene), ULTEM (a polyetherimide), and others. One manufacturing implementation presented in FIG. 5 is a three spherical dome bearing, fabricated with a metallic inner sleeve 14 with three or more receivers, or holes 15, and at least three spheres 16 of ceramic or engineered plastic that can be dropped into holes 15, and an outer backing ring 17 to capture, retain, and lock the three spheres 16 in place. Incorporation of such a bearing cage retainer system that captures preformed ceramic or engineered plastic elements can reduce both machining time required and resulting fabrication cost.

Such a design permits the retainer cage components 14 and 17, which are not contact bearing surfaces, to be manufactured from an easier machinable material, such as but not limited to, metal in simple geometrical forms with well-established and cost effective production techniques. The retainer cage components 14, 17 can be fabricated with a high quality surface finish and held to tight tolerances in order to accurately locate and capture the spheres 16 of ceramic or plastic used as bearing running surfaces. Sphere and journal material pairs are selected and sizing is calculated with respect to P-V values to insure proper load carrying capacity. A radial cross section, shown in FIG. 6, of the bearing assembly incorporating spheres 16 to create spherical domes shows the relative component sizing of the spherical dome versus gap sizing 5.

Figure 7:
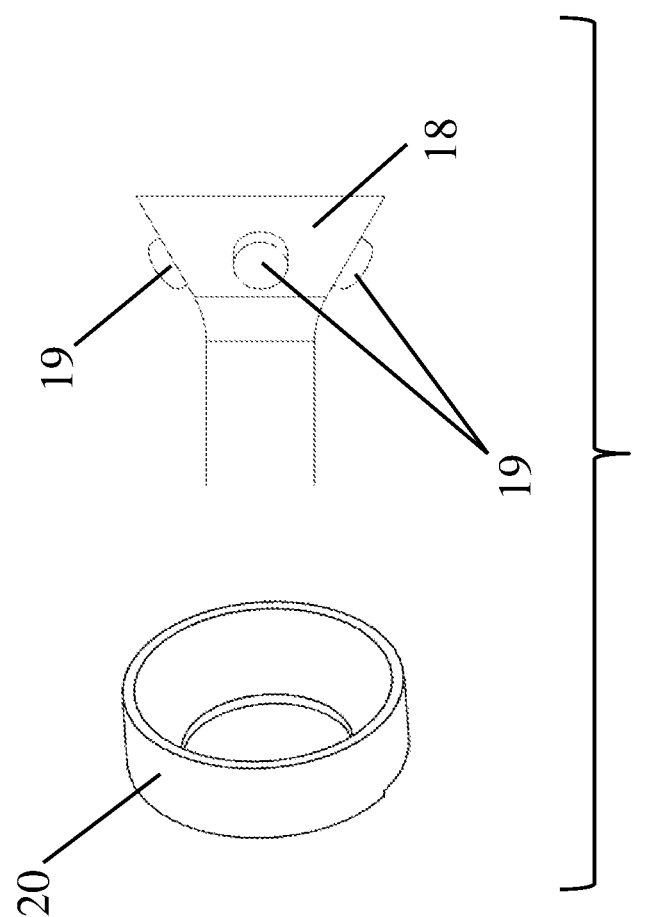
FIG. 7 is an exploded side elevation view of a conical journal and a mating conical bearing with spherical domes.

Another embodiment of the invention, illustrated in FIG. 7, is to incorporate the spherical domes, pins, or stylus shaped protrusions, all represented by cylinders 19, into the non-moving fixed bearing 18, which can be located on the centerline of the blood pump. This situation would be applicable to an out-runner style motor with the stator on the pump axial centerline surrounded by the rotatable rotor fitted with a smooth, conically-shaped journal bore 20. In similar fashion to the multi-material bearing previously discussed, the bearing 18 can be fabricated from metal with at least three receivers, or holes, in the conical surface, while the protrusions can be formed from desirable bearing materials such as ceramic or engineered plastic. Such domes, pins, or styluses are then secured into the bearing by appropriate means, such as press fit, shrink fit, brazing, adhesive, etc.

Figure 9:
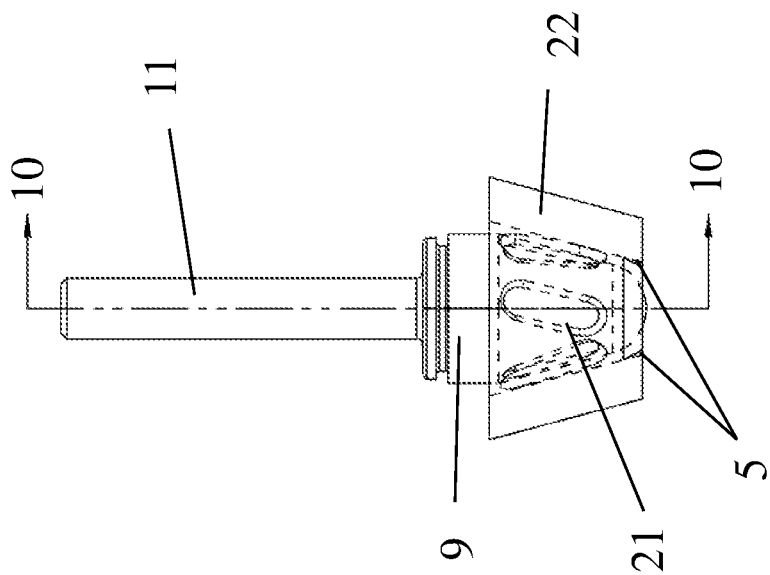
FIG. 9 is a side elevation view of a conical bearing with hemi-cylindrical protruding bearing surfaces set at an angle from the bearing centerline.
Figure 8:
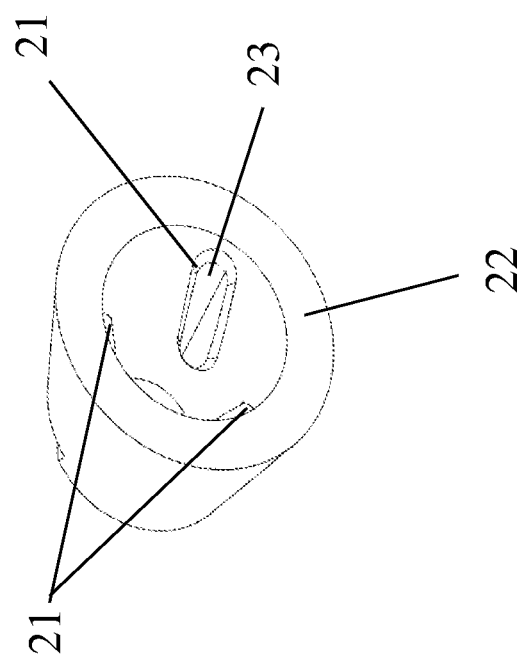
FIG. 8 is a perspective view of a conical bearing with hemi-cylindrical protruding bearing surfaces.

Another embodiment of the invention, illustrated in FIG. 8, is to fabricate cylindrical shaped protrusions 21 into a conical bearing 22. These rod shaped bearing surfaces can be aligned with the centerline as in FIG. 8, or situated at an off-angle as shown in FIG. 9 so the bearing surface augments the pumping capability during rotor rotation. The bearing 22 situated outboard of the stator and would be applicable to an out-runner style motor with the stator on the pump axial centerline, fitted with a smooth conically-shaped journal 9, is surrounded by the rotating, notating, or oscillating moveable member 22. In similar fashion to the multi-material bearing previously discussed, the bearing 22 can be fabricated from metal with at least three receivers, or holes, in the conical surface, while the protrusions can be formed from desirable bearing materials such as ceramic or engineered plastic. Such rods, domes or styluses are then secured into the bearing by appropriate means, such as press fit, shrink fit, brazing, adhesive, etc.

Figure 10:
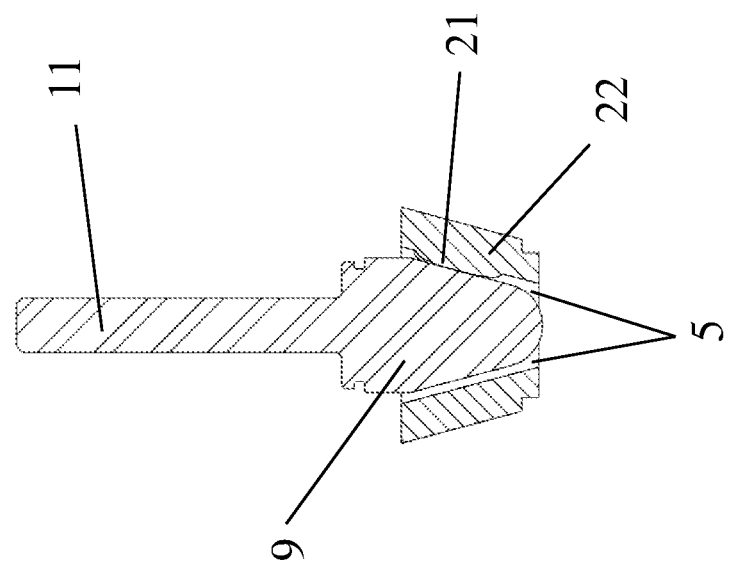
FIG. 10 is an axial cross section of a conical journal and a mating conical bearing with hemi-cylindrical protruding bearing surfaces.

FIG. 9 shows the cylindrical shaped bearing protrusions 21 are offset at an angle to the system's centerline for pumping of the annulus fluid. FIGS. 9 and 10 show the gap 5 between rotating and non-rotating components and a cylindrical protrusion 21.

This bearing concept is also valid for cylindrical shaped bearings that react radial loads and moments. FIG. 11 shows a single piece cylindrical rotor with a multiplicity of formed spherical, pin, or stylus shaped bearing surface protrusions 10, with contact faces 13. A mounting pin 11 can be mechanically attached to the rotor by fasteners, welding, adhesives, or other methods.

Figure 12A:
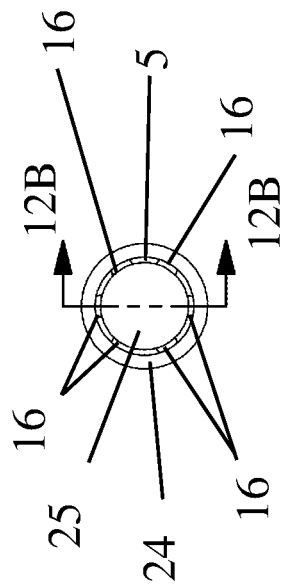
FIG. 12A is an end elevational view of the bearing of FIG. 12.
Figure 12B:
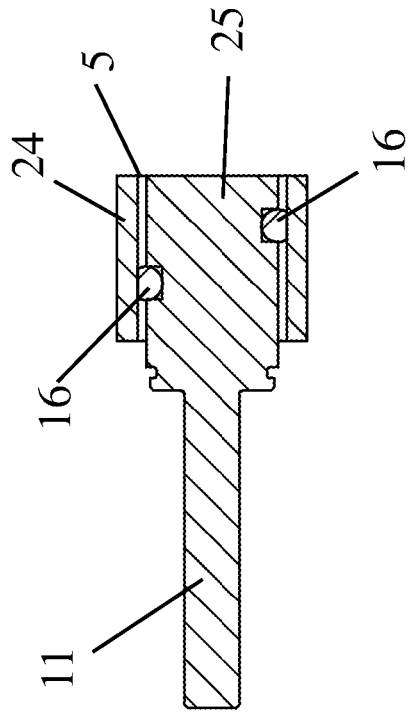
FIG. 12B is a sectional view of the bearing of FIG. 12A, taken along lines 12B-12B of FIG. 12A.
Figure 12:
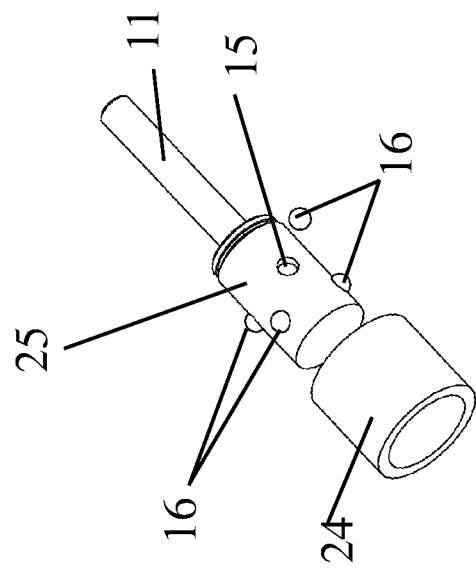
FIG. 12 is an exploded perspective view of a cylindrical bearing fabricated using spheres of ceramic or engineered plastic captured in the holes in the inner bearing component.
Figure 12C:
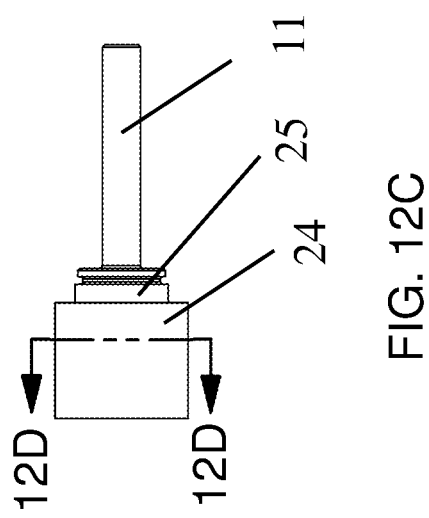
FIG. 12C is a side elevational view of the bearing of FIG. 12.
Figure 12D:
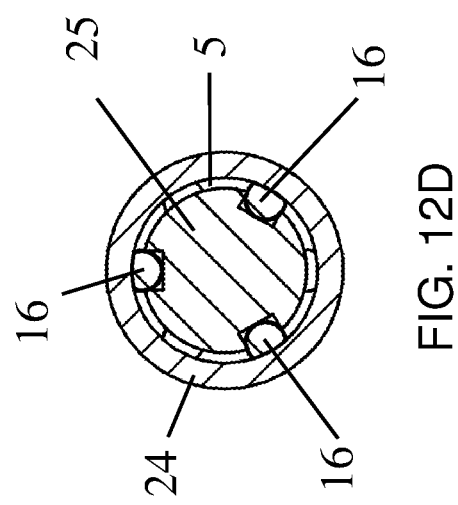
FIG. 12D is a sectional view of the bearing of FIG. 12C taken along lines 12D-12D of FIG. 12C.

FIGS. 12-12D illustrate a cylindrical bearing configuration utilizing spherical bearings elements 16 captured in holes 15 within a central rotor 25, or inner bearing component and secured into the bearing by appropriate means, such as press fit, shrink fit, brazing, adhesive, etc.

Figure 13:
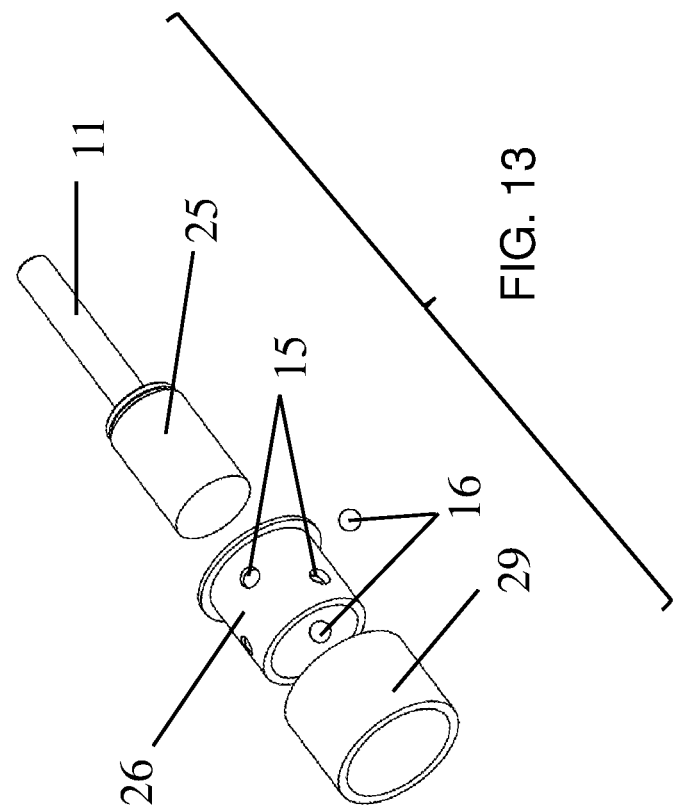
FIG. 13 is an exploded perspective view of a cylindrical bearing fabricated using ceramic or engineered plastic spheres captured in the retainer ring to create the bearing surfaces on the outer bearing component.
Figure 13B:
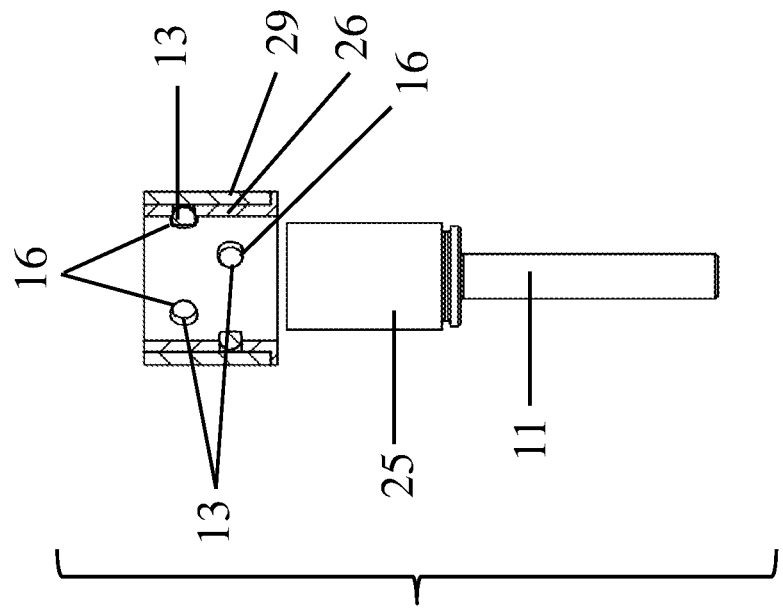
FIG. 13B is a sectional view of the bearing of FIG. 13A taken along lines 13B-13B of FIG. 13A.
Figure 13A:
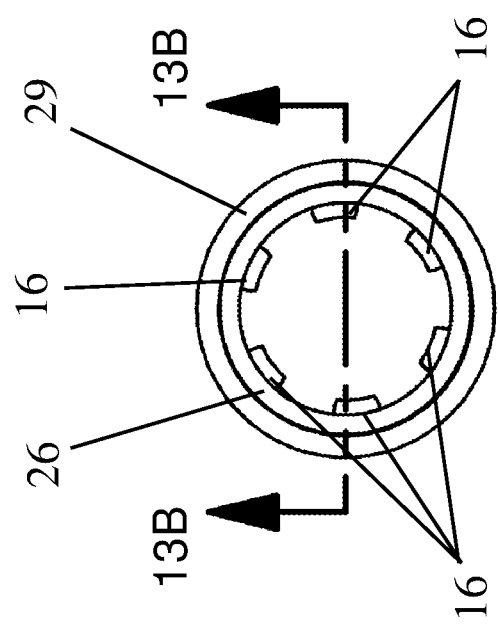
FIG. 13A is an end view of the bearing of FIG. 13.
Figure 14:
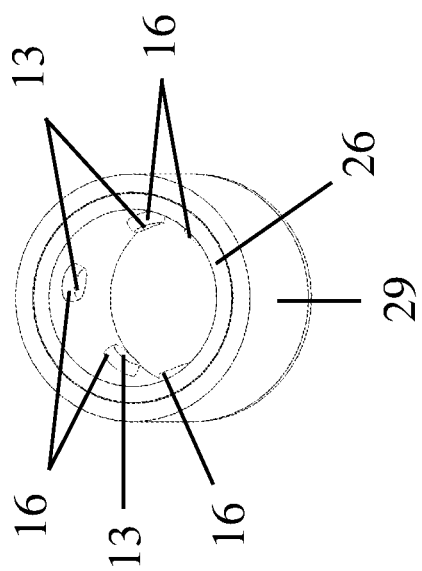
FIG. 14 is a perspective view of the cylindrical bearing interior fabricated using spheres of ceramic or engineered plastic captured in the bearing retainer and by the bearing backing ring.

Conversely, FIGS. 13-13B illustrate a cylindrical bearing configuration utilizing spherical bearings elements 16 captured in holes 15 within the cage 26, which is later captured by the retaining ring 29. In FIG. 14, a perspective end view shows the cage 26, the retaining ring 29 and the spherical bearing protrusions 16, as well as the bearing contact areas or lands 13.

Figure 15:
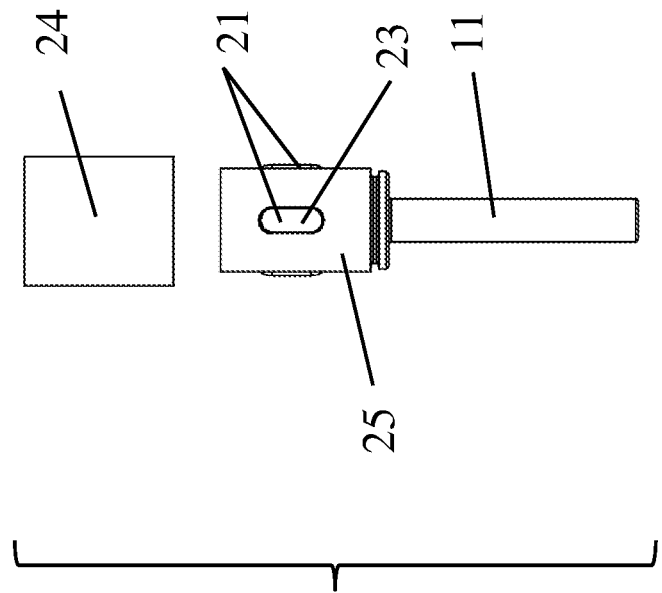
FIG. 15 is an exploded side elevation view of a cylindrical bearing with hemi-cylindrical protruding bearing surfaces on the inner bearing component, which are aligned with the bearing centerline.

The bearing implementations described in this invention can also have a generally cylindrical shape of the bearing components 24, 25 as illustrated in FIG. 15, that provides rotor support for both radial loads and overturning moment resistance, thereby reacting radial hydraulic loads from the pumping action, dead weight loading, centrifugal loads from rotating imbalance, and magnetic loads from rotor/stator mis-alignment. This bearing has axially oriented elongated bearing contact surfaces 23 formed from the hemi-cylindrical protrusions 21 on the inner bearing component.

Figure 17:
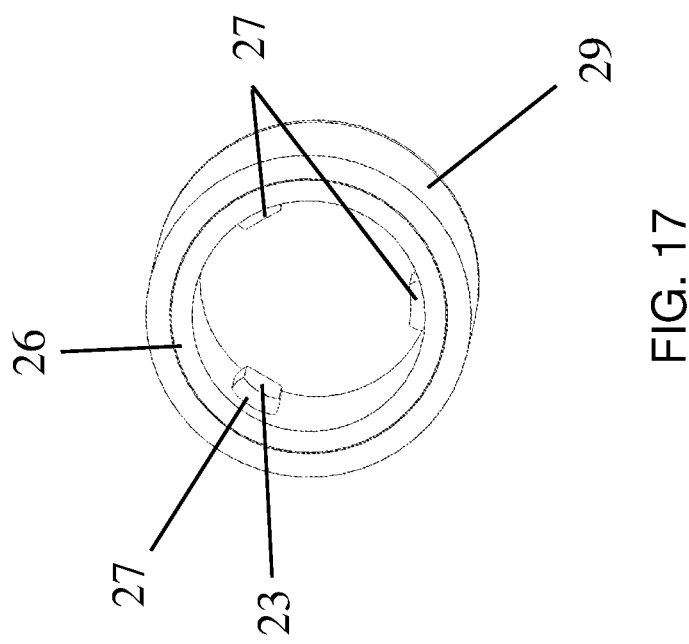
FIG. 17 is a perspective view of the cylindrical bearing interior fabricated using hemi-cylinders of ceramic or engineered plastic captured in the bearing retainer ring and aligned with the bearing centerline.

FIGS. 16-16B illustrate a cylindrical bearing 24 but with the rod shaped cylinders 27 captured within holes 28 of a cage 26 with a retaining ring 29. An axial perspective view in FIG. 17 clearly shows the elongated bearing contact surfaces 23 formed into the cylinders or hemi-cylinders 27 that are captured in cage 26 and backed by the retaining ring 29.

Figure 18:
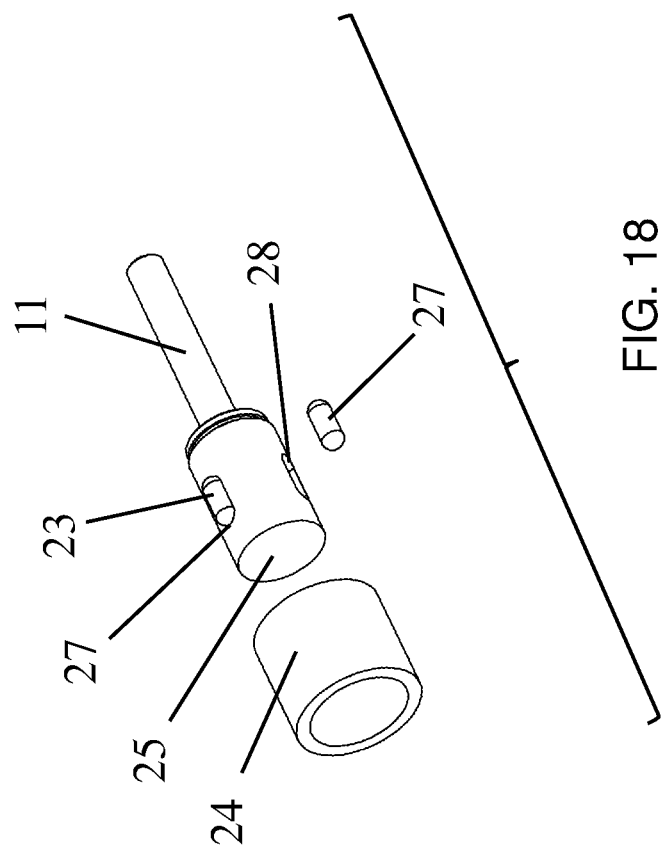
FIG. 18 is an exploded perspective view of a cylindrical bearing fabricated using ceramic or engineered plastic cylinders captured in the retainer ring to create the bearing surfaces on the inner bearing component.
Figure 18B:
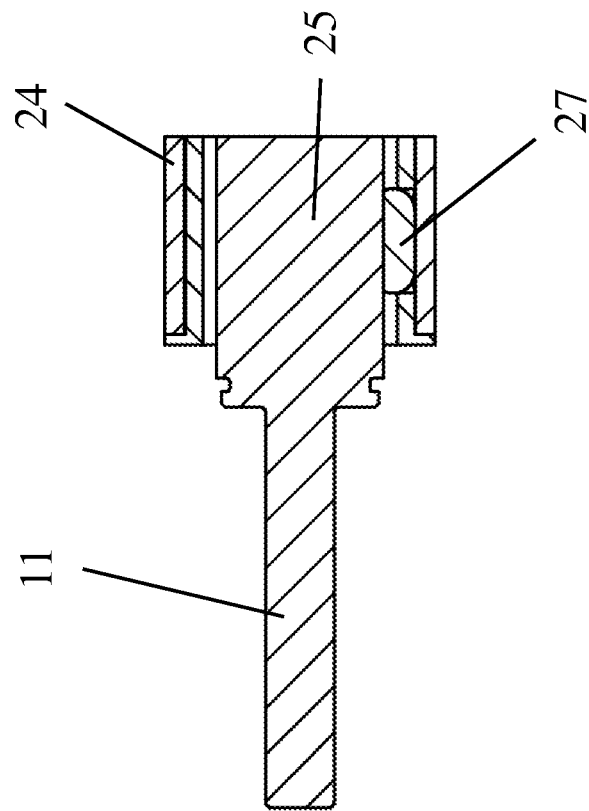
FIG. 18B is a sectional view of the bearing of FIG. 18A taken long lines 18B-18B of FIG. 18A.
Figure 18A:
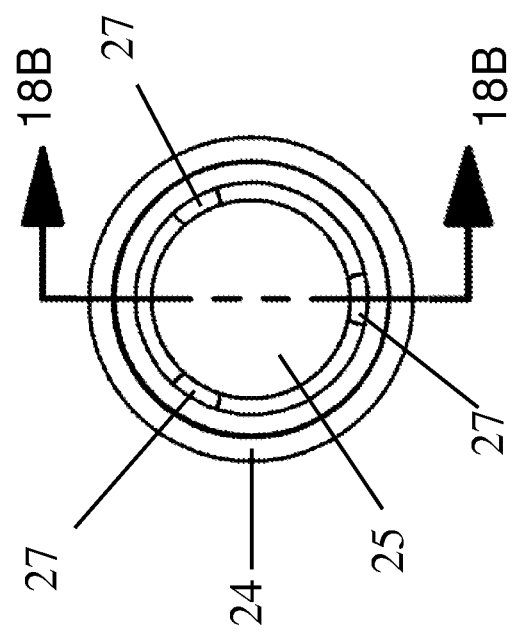
FIG. 18A is an end elevational view of the bearing of FIG. 18.
Figure 18D:
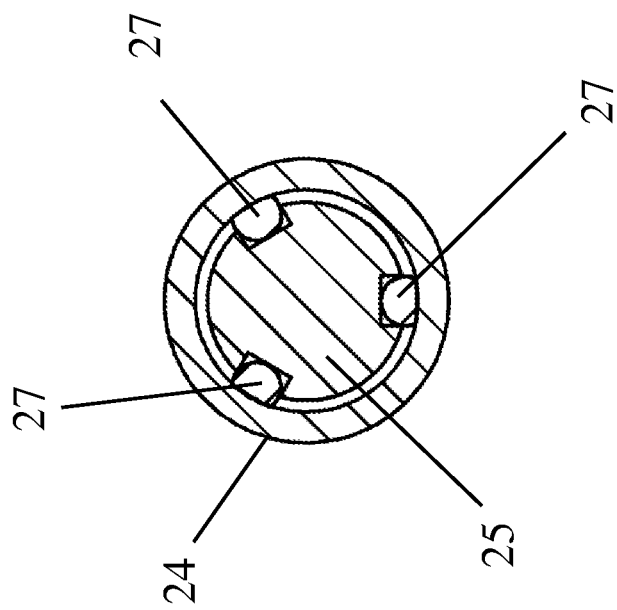
FIG. 18D is a sectional view of the bearing of FIG. 18C taken along lines 18D-18D of FIG. 18C.
Figure 18C:
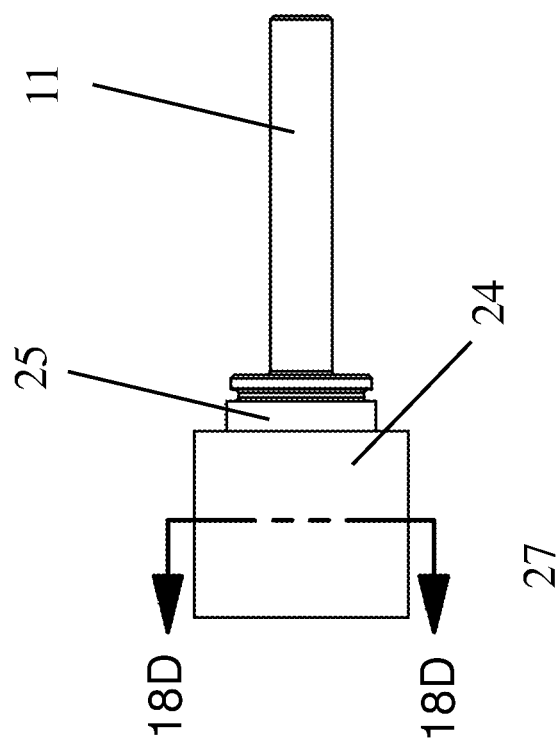
FIG. 18C is a side elevational view of the bearing of FIG. 18.

FIGS. 18-18D show the exploded multi-component multi-material bearing 24,25 with cylindrical rods 27 on the inner bearing component located in holes 28.

It will be further understood that various changes in the details, materials, and arrangements of the parts which have been described and illustrated in order to explain the nature of this invention may be made by those skilled in the art without departing from the scope of the invention as expressed in the following claims.

We claim:

1. A rotor bearing system comprising:
an inner bearing component; and
an outer bearing component,
wherein one of the bearing components includes at least three protrusions sized to form a close running proximity to the remaining component, and
wherein a bearing gap between the inner bearing component and the outer bearing component formed by the protrusions is sized to exclude the entry of red blood cells between the bearing components during operation of the rotor bearing system.

2. The rotor bearing system of claim 1, wherein the protrusions are spherical domes.

3. The rotor bearing system of claim 1, wherein the protrusions are pins.

4. The rotor bearing system of claim 1, wherein the component containing the protrusions is fabricated from a bearing material selected from the group consisting of ceramic, alumina, sapphire, silicon carbide, zirconia, and yttria-stabilized zirconia.

5. The rotor bearing system of claim 1, wherein the component containing the protrusions is fabricated from a bearing material selected from the group consisting of poly ether-ether ketone (PEEK), ultra high molecular weight polyethylene (UHMWPE), polyetherimide (ULTEM), and Polytetrafluoroethylene (PTFE).

6. The rotor bearing system of claim 1, wherein the bearing components are generally conical in shape and react to both radial and axial loads simultaneously.

7. The rotor bearing system of claim 1, wherein the bearing components are generally cylindrical in shape and react to both radial loads and overturning moments simultaneously.

8. The rotor bearing system of claim 1, wherein the bearing component containing the protrusions moves with respect to the other bearing component, the other bearing component being fixed.

9. The rotor bearing system of claim 1, wherein the bearing component containing the protrusions is fixed and wherein the other bearing component moves with respect to the bearing component containing the protrusions.

10. The bearing system of claim 1, wherein the bearing components move in rotation relative to each other.

11. The bearing system of claim 1, wherein the bearing components move in oscillation relative to each other.

12. The bearing system of claim 1, wherein the bearing components move in notation relative to each other.

13. The bearing system of claim 1, wherein the bearing components move in translation relative to each other.

14. The bearing system of claim 1, wherein the protrusions have a dome-shape.

15. The bearing system of claim 1, wherein the protrusions have a hemi-cylindrical shape.

16. The bearing system of claim 1, wherein one of the bearing components includes sleeve having at least three receivers, each receiver configured to receive at least three drop-in components, and an outer backing ring configured to capture and retain the at least three drop-in components.

17. The bearing system of claim 16, wherein the drop-in components comprise spheres made from one of an engineered plastic and ceramic.

18. The bearing system of claim 16, wherein each of the receivers is designed to accept a drop-in pin.

19. The bearing system of claim 16, wherein each of the receivers is designed to accept a drop-in hemisphere.

20. The bearing system of claim 16, wherein each of the receivers is designed to accept a drop-in ellipsoidal dome.

21. The bearing system of claim 16, wherein each of the receivers is designed to accept a drop-in cylinder.

22. The bearing system of claim 16, wherein the drop-in components are generally cylindrical in shape to react to both radial loads and overturning moments simultaneously.

* * * * *